(12) United States Patent
Goeke

(10) Patent No.: US 7,078,570 B2
(45) Date of Patent: Jul. 18, 2006

(54) SUBSTITUTED CYCLOHEXENES

(75) Inventor: Andreas Goeke, Dübendorf (CH)

(73) Assignee: Givaudan SA, Vernier (CH)

(*) Notice: Subject to any disclaimer, the term of this patent is extended or adjusted under 35 U.S.C. 154(b) by 0 days.

(21) Appl. No.: 10/433,342

(22) PCT Filed: Dec. 3, 2001

(86) PCT No.: PCT/EP01/14107

§ 371 (c)(1),
(2), (4) Date: May 23, 2003

(87) PCT Pub. No.: WO02/46131

PCT Pub. Date: Jun. 13, 2002

(65) Prior Publication Data

US 2004/0073050 A1 Apr. 15, 2004

(30) Foreign Application Priority Data

Dec. 5, 2000 (EP) ............................................ 00126655

(51) Int. Cl.
*C07C 45/00* (2006.01)
*C07C 41/00* (2006.01)
*C07C 35/18* (2006.01)
*A61K 7/46* (2006.01)
*A21D 2/00* (2006.01)

(52) U.S. Cl. ....................... 568/362; 568/364; 568/667; 568/823; 512/2; 426/539; 426/590

(58) Field of Classification Search ................ 568/362, 568/364, 667, 823; 512/2; 426/539, 590
See application file for complete search history.

(56) References Cited

U.S. PATENT DOCUMENTS 4,326,996 A * 4/1982 Willis et al. ................... 512/23
4,671,798 A   6/1987 Tarchini ......................... 8/522

FOREIGN PATENT DOCUMENTS

EP          0 167 709        1/1986

OTHER PUBLICATIONS

Miller, Bernard. Acid–Catalyzed Sigmatropic Shifts of Allyl Groups in Cyclohexa–2,4–dien–1–ones. The Possibility of Differing Reactions from n– and pi–Protonated Ketones.☐☐J. Amer. Chem. Soc. vol. 92, (21), 1970, p 6246–6252.*

PCT International Search Report, dated Mar. 6, 2002, for PCT/EP01/14107.
Cornubert, R. et al., "Les combinaisons dites tetrahyropyroniques ont effectivement cette constitution", Bulletin de la Societe Chimique de France, 1933, vol. 53, pp. 619–633.
Chemical Abstracts, vol. 88, no. 13, "Degenerate rearrangement of 1–benzyl–1,2,3,4,5,6–hexamethylbenzonium ion"; XP–002165703.
H.R. Waespe, et al.: "Zur Photochemie von allylarylathern"; Helvetica Chimica Acta, vol. 61, No. 1, Jan. 25, 1978, pp. 401–429, XP002165698; Verlag Helvetica Chimica Acta, Basel, CH; ISSN: 0018–019X; compound 26.
S. Chalais, et al.: "Catalysis of the cyclohexadienone–phenol rearrangement by al Lewis–acidic clay system"; Tetrahedron Letters, vol. 27, No. 23, 1986, pp. 2627–2630, XP002165699; Elsevier Science Publishers, Amsterdam, NL; ISSN: 0040–4039; table 1, entries 2,4.
B. Miller: "Acid–catalysed sigmatropic shifts of allyl groups in cyclohexa–2,4–dien–1–ones. The possibility of differing reactions from n–and pi–protonated ketones"; Journal Of The American Chemical Society, vol. 92, No. 21, Oct. 21, 1970, pp. 6246–6252, XP002165700; American Chemical Society, Washington, DC, US; ISSN: 0002–7863; compound 3.
B. Miller: "Acid–catalysed '1,2! And '1,5! Migrations in linearly conjugated cyclohexadienones. Further evidence for differing types of migration from n–and pi–protonated cyclohexadienones", Journal Of The American Chemical Society, vol. 92, No. 21, Oct. 21, 1971, pp. 6252–6259, XP002165701; American Chemical Society, Washington, DC, US; ISSN: 0002–7863; compounds 9, 10.
B. Miller, et al.: "Hydrogenolysis of carbon–carbon bonds in cyclohexadienones", Journal Of Organic Chemistry, vol. 39, No. 17, Aug. 23, 1974, pp. 2605–2607, XP002165702, American Chemical Society, Washington, DC, US; ISSN: 0022–3263; compound 6.
R. Cornubert, et al.: "Les combinaisons dites tetrahypyroniques ont effectivement cette constitution", Bulletin De La Societe Chimique De France, vol. 53, 1933, pp. 619–633, XP000993017; Société française de chimie, Paris, FR; ISSN: 0037–8968; p. 629, line 7–line 24.

* cited by examiner

*Primary Examiner*—Sikarl A. Witherspoon
(74) *Attorney, Agent, or Firm*—Norris McLaughlin & Marcus PA

(57) ABSTRACT

The present invention relates to substituted cyclohexenes, to their use as well as to their preparation method. These compounds have powerful long lasting natural fruity grapefruit notes with minty and fresh green tonalities.

15 Claims, No Drawings

SUBSTITUTED CYCLOHEXENES

The present invention relates to substituted cyclohexenes, to their use as well as to their method of preparation.

The main disadvantage of organoleptic compounds of natural origin, such as grapefruit oil, is, apart from price and availability, their changing quality and odor as well as flavor characteristics. The compounds of grapefruit oil, which are responsible for the typical odor and flavor are well known: Nootkatone was object of many syntheses and structurally related bicyclic compounds were described in various patents. Nonetheless, nootkatone is still too expensive for many applications and its analogues often lack various facets of the natural product. Sulfur containing compounds like 1-p-menthene-8-thiol have also been used in grapefruit accords. Other compounds in this domain are 4-methoxy-2-methylbutan-2-thiol and 8-mercapto-p-menthone. However, these compounds are chemically and olfactorely non homogenous mixtures and, in addition, are sensitive towards oxidation. A further compound exhibiting a fruity, cassis like odor is described in EP 0 167 709.

It is an object of the present invention to provide compounds having long lasting and natural grapefruit notes accompanied by floral and fresh green aspects.

Further it is an object of the present invention to provide compounds with above organoleptic characteristics which do not contain sulfur.

Further it is an object of the present invention to provide an inexpensive method for preparing such compounds.

It has surprisingly been found that compounds of the general formula (I)

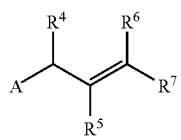

(I)

have powerful long lasting natural fruity grapefruit notes with minty and fresh green tonalities. In compounds of the formula I having less than 18 carbon atoms, A stands for a residue of the formula II, III or IV

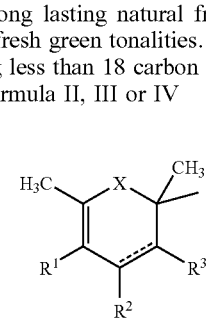

(II)

(III)

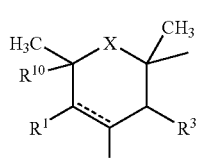

(IV)

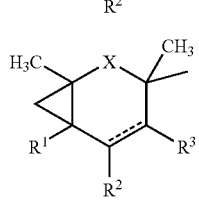

wherein
$R^1$–$R^6$ are independently hydrogen or a methyl group, $R^7$ is a methyl or ethyl group, and $R^5$ and $R^7$ may form together a phenyl ring or a furan;
X is either a carbonyl group or $CR^8OR^9$, wherein $R^8$ is hydrogen, methyl, ethyl, propyl, ethinyl or vinyl and $R^9$ is hydrogen, methyl or ethyl;
$R^{10}$ is hydrogen, methyl or ethyl;
the dotted line in formula (II) is a bond only if X is $CR^8OR^9$; and
the dotted line in formula (III) and the dotted line in formula (IV) optionally is a bond.

The above formula include all possible stereo- and double bond isomers.

Compounds of formula I wherein A is a residue of formula IIa

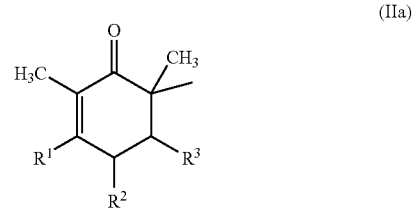

(IIa)

wherein $R^1$–$R^3$ are independently hydrogen or a methyl group are preferred.

Further preferred are compounds of formula I wherein A is a residue of formula IIb

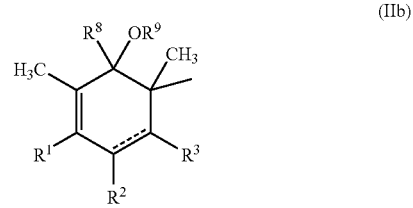

(IIb)

wherein
$R^1$–$R^3$ are independently hydrogen or a methyl group;
$R^8$ is hydrogen, methyl, ethyl, propyl, ethinyl or vinyl and $R^9$ is hydrogen, methyl or ethyl;
and the dotted line in formula (IIb) optionally is a bond.

Especially preferred compounds are:
1,2,6-trimethyl-6-(3-methyl-but-2-enyl)-cyclohex-2-enol,
2,6-dimethyl-6-(3-methyl-but-2-enyl)-cyclohex-2-enol,
2,6-dimethyl-6-(3-methyl-but-2-enyl)-1-vinyl-cyclohex-2-enol,
2,6-dimethyl-1-ethyl-6-(3-methyl-but-2-enyl)-cyclohex-2-enol,
2,6-dimethyl-6-(3-methyl-but-2-enyl)-cyclohex-2-enone,
6-benzyl-2,6-dimethyl-cyclohex-2-enone,
6-methoxy-1,5,6-trimethyl-5-(3-methyl-but-2-enyl)-cyclohexene,
2,2,6-trimethyl-6-(3-methyl-but-2-enyl)-cyclohex-3-enone.

In an organoleptic composition compounds according to the present invention may be used alone or in combination with numerous fragrance or flavor ingredients of natural and/or synthetic origin. The range of the natural fragrances or flavors includes in addition to readily volatile, also moderately and only slightly volatile components. The synthetic fragrances or flavors embrace representatives from practically all classes of fragrance or flavor substances. The following list comprises examples of known fragrances or flavors which may be combined with the compounds of the invention:

natural products: tree moss absolute, basil oil, tropical fruit oils (such as bergamot oil, mandarin oil, etc.), mastix absolute, myrtle oil, palmarosa oil, patchouli oil, petitgrain oil, wormwood oil, lavender oil, rose oil, jasmin oil, ylang-ylang oil, etc.;

alcohols: farnesol, geraniol, linalool, nerol, phenylethyl alcohol, rhodinol, cinnamic alcohol, (Z)-hex-3-en-1-ol, menthol, α-terpineol, etc.;

aldehydes: citral, α-hexyl cinnamaldehyde, Lilial, methylionone, verbenone, nootkatone, geranylacetone, etc.;

Compositions comprising one or more compounds according to the present invention are preferably used in consumer products and industrial products. A few examples are body care and cosmetic products such as cream, shampoo, soap, sun cream, household products such as detergent, household cleaner, fabric softener, etc.

In a preferred embodiment food and beverage products comprise one or more compounds according to the present invention.

Compounds according to the present invention can be prepared as depicted in scheme 1 and 2.

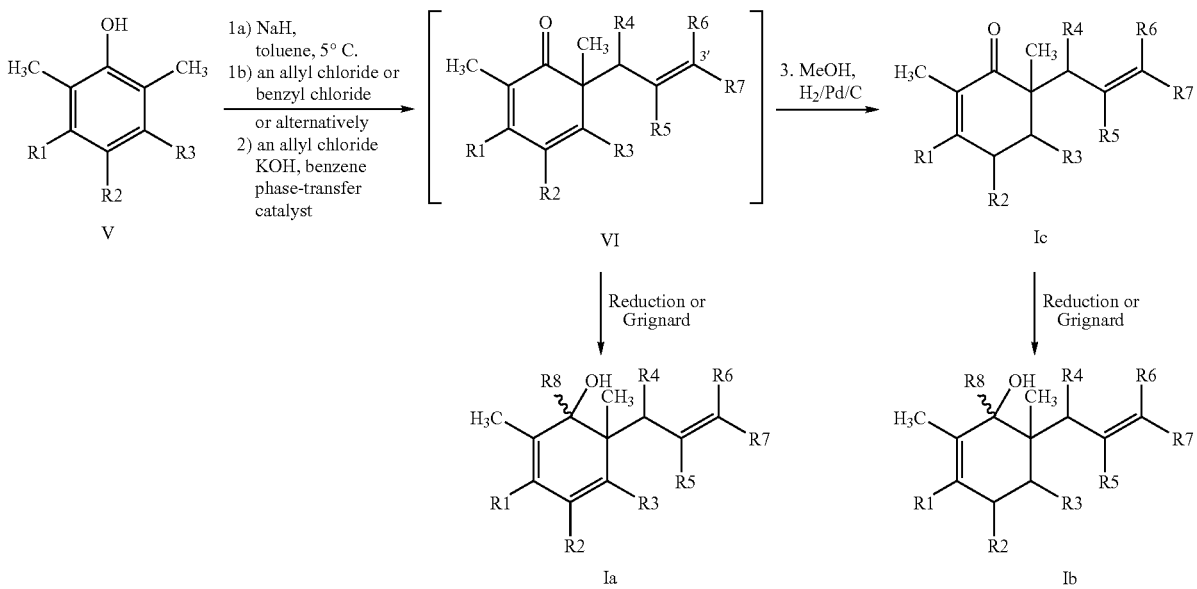

Scheme 1:

esters: allyl phenoxyacetate, benzyl salicylate, cinnamyl propionate, citronellyl acetate, decyl acetate, dimethylbenzylcarbinyl acetate, dimethylbenzylcarbinyl butyrate, ethyl acetoacetate, cis-3-hexenyl isobutyrate, cis-3-hexenyl salicylate, linalyl acetate, methyl dihydrojasmonate, styralyl propionate, vetiveryl acetate, benzyl acetate, geranyl acetate, etc.;

lactones: γ-undecalactone, δ-decalactone, pentadecanolide, 12-oxahexadecanolide, etc.;

acetals: Viridine (phenylacetaldehyde dimethylacetal), etc.;

other components often used in perfumery: indole, p-mentha-8-thiol-3-one, methyleugenol, eugenol, anethol, etc.

The compounds of the present invention harmonize particularly well with floral notes (lily of the valley, rose, iris, jasmine, ylang-ylang, narcissus notes, etc.) as well as with woody, chypre and animalic notes, tobacco- and an patchouli-like compositions, etc.

The percentage in which the compounds of the invention are used in a composition may vary within wide limits ranging from a few parts per thousand in mass market products (e.g. cleaning compositions, deodorant, etc.) up to a few percents in alcoholic extracts for fine perfumery. In all cases, the compounds of formula I provide fragrance compositions with powerful long lasting natural fruity grapefruit notes and minty and fresh green tonalities. Flavoured products comprise compounds according to the present invention at a concentration of 0.1 to 10 ppm.

C-Alkylations of 2,6-disubstituted phenols by reaction of a phenol with a metal hydride and an alkenylchloride are known in the art (Greuter, H. et al. (1977) *Helv. Chim. Acta*, 60, 1701). The resulting dienones are known to be unstable and to rearrange to higher alkylated phenols, or to arylalkenyl-ethers, or the allyl unit may also be cleaved off under certain reaction conditions known to those skilled in the art (Chalais, S. et al. (1986) *Tetrahedron Lett*., 27, 2627).

The alkylation for preparing the compounds of the present invention can also be performed under phase-transfer conditions, which avoids the use of the expensive metal hydride. It was surprisingly found, that the intermediate dienones of the formula VI of scheme 1 can be selectively hydrogenated with a transition metal catalyst, instead of generating the above mentioned side products. A preferred transition metal catalyst is palladium on charcoal. This hydrogenation is especially efficient for substrates of scheme 1 wherein the 3'-position ($R^6$ and $R^7$) is dialkylated, or for substrates of scheme 1 wherein $R^5$ and $R^7$ constitute an aromatic ring.

The α, β-unsaturated ketones of the formula Ic may be converted to cyclohexenol derivatives of the formula Ib. Depending on number and location of substituents on the cyclohexene ring, 2 or more diastereomeric alcohols may be formed. For example, 1,2,6-trimethyl-6-(3-methyl-but-2-enyl)-cyclohexenol consists of 2 isomers, one having a borneol/grapefruit character with a GC threshold of 18 ng/L, the other having a grapefruit/cassis note with an odor threshold of 0.5 ng/L.

The unsaturated ketones of the formula VI may be converted to cyclohexadienol derivatives of the formula Ia according to the process illustrated in scheme 1.

In addition, compounds of the formula Ic and of the formula Ib (scheme 1) may further be converted as described in scheme 2.

Scheme 2:

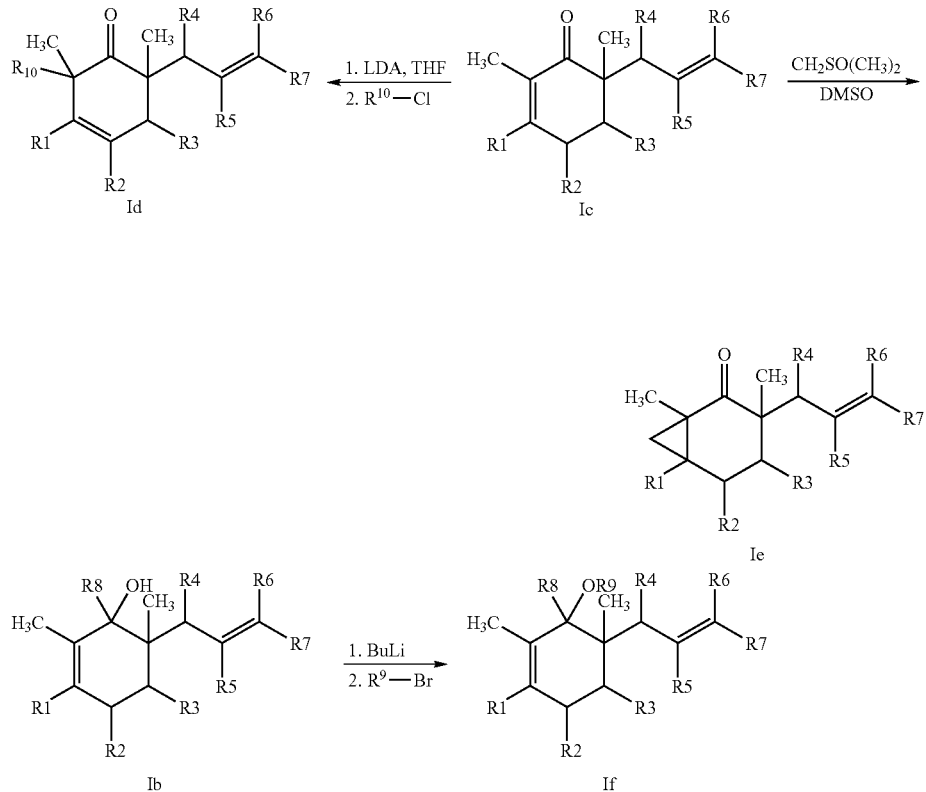

The invention will be further described, by way of illustration, in the following examples.

All compounds were unambiguously identified by their $^1$H-NMR-(chemical shifts ($\delta$) are given in ppm downfield from TMS; coupling constants J in Hz), IR- and MS-spectra.

EXAMPLE 1

Synthesis of 2,6-dimethyl-6-(3-methyl-but-2-enyl)-cyclohex-2-enone

Odor: fruity, grapefruit, minty, bergamot

Sodium hydride (60%, 85 g, 2.13 mol) was added portionwise to a solution of 2,6-dimethylphenol (250 g, 2.05 mol) in 2 L of toluene at 10–15° C. The resulting suspension was stirred for 45 min. The mixture was cooled to 50° C., and prenyl chloride (262 g, 2.13 mol, 85%) was added during 1.5 h keeping the temperature at 50° C. The mixture was then stirred for further 2 h at 10–15° C. Methanol (1 L) and palladium (2.5 g, 10% on charcoal) was added and the grey suspension was hydrogenated at 0.3 bar overpressure, keeping the temperature at 20–22° C. (ice bath). The suspension was then filtered through a pad of celite. The yellow filtrate was washed with water (0.5 L), aqueous sodium hydroxide (0.5 L) and brine (0.5 L), dried (MgSO$_4$) and concentrated in vacuo. The residue was distilled over a 5 cm Vigreux column to yield 318 g (81%, bp 78–82° C./0.05 Torr) of a colorless oil. $^1$H-NMR (400 MHz, CDCl$_3$): 6.62 (bs, 1H, 3-H), 5.06–5.11 (m, 1H, 2'-H), 2.34–2.28 (m, 2H, 4-H), 2.25–2.14 (m, 2H, 1'H), 1.91 (dt, $J_{5a,5b}$=13.6 Hz, $J_{5a,4}$=6.1 Hz, 1H, 5$_a$-H), 1.76 (s, 3H, 2-CH$_3$), 1.77–1.70 (m, 1H, 5$_b$-H), 1.70 (s, 3H, 4'-CH$_3$), 1.59 (s, 3H, 3'-CH$_3$), 1.05 (s, 3H, 6-CH$_3$) ppm. GC/MS (EI): 192 (M$^+$, 16), 124 (100), 109 (74), 82 (31), 69 (40), 41 (57). IR (ATR): 2965s, 2922s, 1667vs, 1449m, 1376m, 1033m cm$^{-1}$.

EXAMPLE 2

2,4,6-Trimethyl-6-(3-methyl-but-2-enyl)-cyclohex-2-enone

Odor: hesperidic, fresh, floral, grapefruit, terpenic

Mixture of 2 diastereomers in a ratio of 4/1: $^1$H-NMR (400 MHz, CDCl$_3$): 6.43 (bs, 1H, 3-H), 5.09–5.03 (m, 1H, 2'-H), 2.62–2.52 (m, 1H, 4-H), 2.36–2.11 (m, 2H, 1'-H), 1.76 (s, 3H, 2-CH$_3$), 1.71–1.67 (m, 1H, 5$_a$-H), 1.68 (s, 3H, 4'-CH$_3$), 1.61 (s, 3H, 3'-CH$_3$), 1.59–1.55 (m, 1H, 5$_b$-H), 1.09 (d, J=6.8 Hz, 3H, 4-CH$_3$), 1.07/1.03 (2s,3H, 6$_{a,b}$-CH$_3$) ppm. GC/MS (EI), main isomer: 206 (M$^+$, 13), 164 (20), 138 (69), 123 (100), 96 (27), 69 (35), 41 (81). IR (ATR): 2962s, 2924s, 1670vs, 1453s, 1376s, 1035m, 986m cm$^{-1}$.

EXAMPLE 3

2,3,6-Trimethyl-6-(3-methyl-but-2-enyl)-cyclohex-2-enone

Odor: agrestic, minty, fruity $^1$H-NMR (400 MHz, CDCl$_3$): 5.09–5.05 (m, 1H, 2'-H), 2.33–2.29 (m, 2H, 4-H), 2.25–2.11 (m, 2H, 1'-H), 1.89 (s, 3H), 1.89–1.83 (m, 1H, 5$_a$-H), 1.75 (s, 3H), 1.70 (s, 3H), 1.69–1.63 (m, 1H, 5$_b$-H), 1.59 (s, 3H), 1.03 (s, 3H, 6-CH$_3$) ppm. GC/MS (EI): 206 (M$^+$, 9), 178 (15), 138 (100), 137 (98), 123 (97), 96 (50), 67 (52), 41 (62). IR (ATR): 2915s, 1659vs, 1638s, 1376s, 1023m, 764w cm$^{-1}$.

EXAMPLE 4

6-Benzyl-2,6-dimethyl-cyclohex-2-enone

Odor: Fruity, minty, saffron, rosy, apple.

$^1$H-NMR (200 MHz, CDCl$_3$): 7.28–7.09 (m, 5H, Ar—H), 6.65 (bs, 1H, 3-H), 2.97 (d, J=15 Hz, 1H, CH$_a$HPh), 2.74 (d, J=15 Hz, CHH$_b$Ph), 2.40–2.29 (m, 2H, 4-H), 1.91–1.60 (m, 2H, 5-H), 1.06 (s, 3H, 6-H) ppm. GC/MS (EI): 214 (M⁺, 27), 186 (37), 123 (44), 95 (13), 91 (100), 82 (91), 77 (10), 65 (18), 54 (25), 39 (20). IR (ATR): 2923s, 1666vs, 1452s, 1375m, 1027m, 702s cm$^{-1}$.

EXAMPLE 5

Synthesis of 1,3-dimethyl-3-(3-methyl-but-2-enyl)-bicyclo[4.1.0]heptan-2-one

Odor: rosy, vetiver, saffron, floral

Sodium hydride (60%, 2.11 g, 52.8 mmol) was added to a suspension of trimethylsulfoxonium iodide (11.6 g, 52.8 mmol) in 60 ml of dimethyl sulfoxide. The mixture was stirred for 30 min until hydrogen evolution stopped. 2,6-Dimethyl-6-(3-methyl-but-2-enyl)-cyclohex-2-enone was added and the mixture was stirred over night at room temperature, was then diluted with water and extracted with pentane. The organic phase was washed with water and brine, dried (MgSO₄) and concentrated in vacuo. The residue was distilled (bp.95° C./0.05 Torr) to yield 4.5 g (83%) of product as a mixture of two diastereomers. ¹H-NMR (200 MHz, CDCl₃): 5.11–4.93 (m, 1H, 2'-H), 2.45–1.32 (m, 7H), 1.75/1.70 (2s, 3H, 4'H), 1.63/1.59 (2s, 3H, 3'-CH₃), 1.31–1.16 (m, 1H), 1.23/1.21 (2s, 3H), 1.01/0.99 (2s, 3H), 0.75–0.64 (m, 1H) ppm. GC/MS (EI): 206 (M⁺, 12), 191 (14), 163 (20), 138 (90), 123 (100), 109 (34), 95 (57), 69 (62), 41 (94). IR (ATR): 2962s, 2928s, 2866s, 1681vs, 1451s, 1375m, 1043m, 1000m cm$^{-1}$.

EXAMPLE 6

Synthesis of 2,2,6-trimethyl-6-(3-methyl-but-2-enyl)-cyclohex-3-enone

Odor: grapefruit, sage, saffron, lavander 2,6-Dimethyl-6-(3-methyl-but-2-enyl)-cyclohex-2-enone (5.00 g, 26 mmol) was added to a solution of LDA (prepared from diisopropylamine (3.15 g, 31.2 mmol) and n-BuLi (1.6M in hexane, 19.5 ml, 31.2 mmol)) in THF (50 ml) at −78° C. The mixture was stirred for 1 h at −78° C. Methyl iodide (5.54 g, 39 mmol) was added and the solution was allowed to warm to room temperature over night. The mixture was diluted with MTBE and washed with portions of H₂O and brine, dried (MgSO₄) and concentrated in vacuo to yield 7 g of a slightly yellow oil which was distilled (bp.42° C./0.005 mbar) to give 4.5 g (84%) of an olfactorily clean oil. ¹H-NMR (400 MHz, CDCl₃): 5.72–5.68 (m, 1H), 5.63–5.59 (m, 1H), 5.06–4.99 (m, 1H), 2.36–2.08 (m, 4H), 1.70 (s, 3H), 1.59 (s, 3H), 1.15 (s, 3H), 1.12 (s, 3H), 1.07 (s, 3H) ppm. GC/MS (EI): 206 (M⁺, 15), 191 (8), 137 (19), 123 (25), 109 (100), 96 (34), 91 (9), 81 (28), 67 (24), 41 (33). IR (ATR): 3023s, 2966s, 2926m, 1703vs, 1456s, 1376m, 1203w, 1033s, 713s cm$^{-1}$.

EXAMPLE 7

2,6-Dimethyl-2-(3-methyl-but-2-enyl)-cyclohexanone

Odor: grapefruit, rosy

This compound was prepared as a mixture of 2 isomers by reduction of 2,6-dimethyl-6-(3-methyl-but-2-enyl)-cyclohex-2-enone with Na₂S₂O₄. ¹H-NMR (400 MHz, CDCl₃): 5.15–5.12, 4.94–4.89 (2m, 1H, 2'-H), 2.69–1.26 (m, 9H), 1.70, 1.68 (2s, 3H, 3'-CH₃), 1.61, 1.60 (2s, 3H, 4'-H), 1.47, 0.98 (2s, 3H, 6-CH₃), 1.00, 0.99 (2d, J=6.8 Hz, 2-CH₃) ppm. MS (EI): 194 (M⁺, 19), 179 (17), 126 (100), 111 (52), 95 (26), 69 (72), 55 (39), 41 (56). IR (ATR): 2967m, 2929s, 2868s, 1705vs, 1452s, 1376m, 995m cm$^{-1}$.

EXAMPLE 8

Synthesis of 1,2,6-trimethyl-6-(3-methyl-but-2-enyl)-cyclohex-2-enol

Odor: grapefruit, cassis, borneol 2,6-Dimethyl-6-(3-methyl-but-2-enyl)-cyclohexenone (245 g, 1.28 mol) was added dropwise to a solution of methyl magnesium chloride (105 g, 1.41 mol) in THF (400 ml) and toluene (1.5 L) at room temperature. The temperature rose to 50° C. The mixture was stirred for additional 45 min, was then cooled to 15° C. and poured on ice. The organic phase was separated and washed with water (0.5 L) and brine (0.5 L), dried (MgSO₄) and concentrated in vacuo. The residue was distilled over a 70 cm silverplated column (bp. 83–85° C./0.1 Torr) to yield 208 g (78%) product as a mixture of two diastereomers. ¹H-NMR (400 MHz, CDCl₃): 5.39 (bs, 1H, 3-H), 5.29–5.24 (m, 1H, 2'-H), 2.26–2.05 (m, 2H, 2'-H), 1.98–1.88 (m, 2H, 4-H), 1.75–1.71 (m, 6H, 2-CH₃, 3'-CH₃), 1.63 (s, 3H, 4'-H), 1.60 (bs, 1H, O—H), 1.50–1.46 (m, 2H, 5-H), 1.24/1.23 (2s, 3H, 1$_{a,b}$-CH₃), 0.96/0.90 (2s, 3H, 6$_{a,b}$-CH₃) ppm. GC/MS (EI), Isomer a: 208 (M⁺, 1), 190 (20), 175 (17), 147 (56), 121 (100), 105 (46), 98 (52), 83 (45), 43 (82). Isomer b: 208 (M+, 2), 190 (8), 175 (6), 147 (58), 121 (75), 105 (46), 98 (100), 83 (52), 43 (78). IR (ATR): 3476s, 2967vs, 2922vs, 1450s, 1376s, 1073vs, 921m, 902 m cm$^{-1}$.

EXAMPLE 9

Synthesis of 6-methoxy-1,5,6-trimethyl-5-(3-methyl-but-2-enyl)-cyclohexene

Odor: grapefruit, agrestic, borneol, sage, lavander, lime, cassis

To a solution of 1,2,6-trimethyl-6-(3-methyl-but-2-enyl)-cyclohex-2-enol (5.00 g, 24.0 mmol) in THF (80 ml) was added n-BuLi (1.6M in hexane, 16.5 ml, 26.4 mmol) at 0° C. After the mixture was stirred for 30 min, methyl iodide (5.18 g, 36.5 mmol) was added. The mixture was stirred at room temperature over night and then poured on ice and extracted with MTBE. The organic phase was washed with H₂O and brine, dried (MgSO₄) and concentrated in vacuo. The residue was distilled (bp. 75° C./0.2 Torr) to yield 5.0 g (93%) of a colorless oil containing 2 isomers: ¹H-NMR (400 MHz, CDCl₃): 5.64 (bs, 1H, 2-H), 5.23–5.15 (m, 1H, CH₂CH=C(CH₃)₂), 3.30, 3.28 (2s, 3H, O—CH₃), 2.22–2.12 (m, 1H), 1.99–1.88 (m, 3H), 1.75–1.58 (m, 10H), 1.20, 1.18 (2s, 3H), 0.93, 0.79 (2s, 3H) ppm. MS (EI): 222 (M⁺, 1), 190 (11), 175 (10), 147 (60), 121 (100), 112 (30), 105 (57), 91 (40), 79 (25), 69 (14), 41 (45). IR (ATR): 2966s, 2926s, 1449s, 1377s, 1083vs, 858m cm$^{-1}$.

EXAMPLE 10

1,2,4,6-Tetramethyl-6-(3-methyl-but-2-enyl)-cyclohex-2-enol

Odor: earthy, hesperidic, rosy, woody, grapefruit

Two diastereomers in a ratio of 5/1. Main isomer: ¹H-NMR (400 MHz, CDCl₃): 5.37–5.32 (m, 1H, 2'-H), 5.18 (bs, 1H, 3-H), 2.25 (dd, J$_{gem}$=14.2 Hz, J$_{vic}$=8.2 Hz, 1H, 1'-Ha), 2.20–2.10 (m, 1H, 4-H), 1.90 (dd, J$_{gem}$=14.2 Hz, J$_{vic}$=7.2 Hz, 1H, 1'Hb), 1.73 (s, 3H, 4'H), 1.72 (bs, 3H, 2-H), 1.64 (s, 3H, 3'-CH₃), 1.55 (ddd, J=13.5, 6.0, 1.6 Hz, 1H, 5-Ha), 1.255 (s, 3H, 1-CH₃), 1.12 (dd, J=13.5, 11.0 Hz, 1H, 5-Hb), 0.97 (s, 3H, 6-CH₃), 0.92 (d, J=6.8 Hz, 3H, 4-CH₃) ppm. GC/MS (EI): 222 (M⁺, 1), 207 (18), 161 (50%), 135 (90), 119 (48), 109 (66), 91 (36), 69 (36), 43 (100). IR (ATR): 3491s, 3953vs, 2917vs, 1704m, 1451vs, 1375vs, 1107vs, 1030s, 919s, 836s cm$^{-1}$.

EXAMPLE 11

2,6-Dimethyl-6-(3-methyl-but-2-enyl)-1-vinyl-cyclohex-2-enol

Odor: borneol, grapefruit, cassis, earthy

Two isomers in a ratio of 3/2: ¹H-NMR (200 MHz, CDCl₃): 6.02–5.82 (m, 1H, CHCH₂), 5.05/5.49 (2bs, 1H, 3-H), 5.31–5.15 (m, 3H, 2'-H, CHCH₂), 2.3–1.48 (m, 16H), 0.98/0.87 (2s, 3H, 6-CH₃) ppm. GC/MS (EI) isomer a: 220

(M+, 3), 202 (12), 133 (21), 110 (58), 95 (100), 67 (22), 55 (48), 41 (40). Isomer b: 220 (M+, 2), 202 (6), 133 (10), 110 (74), 95 (100), 69 (14), 55 (44), 41 (34). IR (ATR): 3511s, 2966vs, 2925vs, 1451s, 1375s, 1122m, 994s, 922s cm$^{-1}$.

EXAMPLE 12
2,6-Dimethyl-1-ethyl-6-(3-methyl-but-2-enyl)-cyclohex-2-enol

Odor: earthy, minty, floral, grapefruit

Two isomers in a ratio of 3/2: $^1$H-NMR (200 MHz, CDCl$_3$): 5.48 (bs, 1H, 3-H), 5.39–5.25 (m, 1H, 2'-H), 2.38–2.21 (m, 1H), 2.05–1.85 (m, 3H), 1.76–1.56 (m, 13H), 1.51–1.36 (m, 1H), 1.01–0.89 (m, 6H, CH$_2$CH$_3$, 6-CH$_3$) ppm. GC/MS (EI) isomer a: 222 (M+, 2), 204 (4), 193 (79), 135 (23), 123 (30), 112 (70), 107 (43), 83 (100), 69 (59), 57 (49), 41 (50). Isomer b: 222 (M$^+$, 2), 204 (4), 193 (79), 135 (23), 123 (30), 112 (70), 107 (43), 83 (100), 69 (59), 57 (49), 41 (50). IR (ATR): 3521s, 2965vs, 2926vs, 2880s, 1452s, 1376s, 981s cm$^{-1}$.

EXAMPLE 13
1,2,3-Trimethyl-3-(3-methyl-but-2-enyl)-bicyclo[4.1.0]heptan-2-ol Odor: minty, rhubarb, agrestic Mixture of two diastereomers in a ratio of 3/2: $^1$H-NMR (200 MHz, CDCl$_3$): 5.05–4.90 (m, 1H, 2'-H), 2.05–1.16 (m, 5H), 1.48/1.47 (2s, 3H, 4'-H), 1.38/1.33 (2s, 3H, 3'-CH$_3$), 1.01–0.52 (m, 3H), 0.90/0.88 (2s, 3H), 0.77/0.75 (2s, 3H), 0.65/0.50 (2s, 3H), 0.07-(-1.85) (m, 2H) ppm. GC/MS (EI): 222 (M+, 2), 204 (4), 161 (12), 135 (28), 112 (62), 93 (60), 69 (60), 43 (100), 41 (64). IR (ATR): 3519 s, 2967vs, 2925vs, 2866vs, 1445s, 1375s, 1093m, 918m cm$^{-1}$.

EXAMPLE 14
Synthesis of 2,6-dimethyl-6-(3-methyl-but-2-enyl)-cyclohex-2-enol Odor: grapefruit, vetiver, rhubarb, rosy 2,6-Dimethyl-6-(3-methyl-but-2-enyl)-cyclohex-2-enone (5.00 g, 26.04 mmol) was added dropwise to a suspension of lithium aluminium hydride (0.73 g, 18.2 mmol) in diethyl ether at 0° C. The mixture was stirred at room temperature for 1 h. The resulting suspension was quenched with water, aqueous sodium hydroxide solution and again water, was then filtered and concentrated in vacuo. The residue was distilled (bp. 110° C./0.1 Torr) to yield 4.93 g (98%) of the alcohol as a mixture of 2 diastereomers. $^1$H-NMR (200 MHz, CDCl$_3$): 5.49 (bs, 1H, 3-H), 5.34–5.15 (m, 1H, 2'-H), 3.57/3.44 (2d, J=4.5, 5.5 Hz, 1H, 1-H), 2.25–1.82 (m, 4H), 1.81–1.71 (m, 6H), 1.65/1.61 (2s, 3H), 1.62–1.19 (m, 3H), 0.93/0.82 (2s, 3H, 6-CH$_3$) ppm. GC/MS (EI) isomer a: 194 (M+, 4), 176 (44), 161 (42), 125 (12), 107 (94), 84 (70), 69 (38), 55 (50), 43 (100). IR (ATR): 3365s, 2966s, 2916vs, 1450s, 1375s, 1239m, 1030m, 1007 s cm$^{-1}$.

EXAMPLE 15
2,6-Dimethyl-6-(3-methyl-but-2-enyl)-cyclohexa-2,4-dienone

A mixture of 2,6-dimethylphenol (5.00 g, 41.0 mmol), powdered KOH (85%, 1.5 eq., 4.05 g, 61.5 mmol), prenyl chloride (85%, 1.2 eq., 6.05 g, 49.2 mmol) and (NBu$_4$)HSO$_4$ (50 mg) in benzene (50 ml) was stirred at 0° C. for 3 h. The green suspension was then poured on ice and extracted with pentane. The organic phase was washed with aqueous NaOH (32%), water and brine, dried (MgSO$_4$) and concentrated in vacuo at room temperature. The yellow crude dienone was ca. 85% pure and was converted without further purification. $^1$H-NMR (400 MHz, CDCl$_3$): 6.81–6.79 (m, 1H), 6.20–10 (m, 2H), 4.92–4.88 (m, 1H, 2'-H), 2.51 (dd, J=13.9, 7.7 Hz, 1H, 1'-Ha), 2.17 (dd, J=13.9, 7.2 Hz, 1H, 1'-Hb), 1.86 (s, 3H), 1.62 (s, 3H), 1.57 (s, 3H), 1.17 (s, 3H, 6-CH$_3$) ppm.

EXAMPLE 16
1,2,6-Trimethyl-6-(3-methyl-but-2-enyl)-cyclohexa-2,4-dienol

Odor: grapefruit, hesperidic, floral, terpenic $^1$H-NMR (400 MHz, CDCl$_3$): 5.69 (dd, J=9.3, 5.2 Hz, 1H) 5.56 (dt, J=5.2, 1.5 Hz, 1H), 5.48 (dq, J=9.3, 0.5 Hz, 1H), 5.27–5.20 (m, 1H, 2'-H), 2.32 (dd, J=14.0, 7.1 Hz, 1H, 1'-Ha), 2.17 (dd, J=14.0, 8.4 Hz, 1H, 1'-Hb), 1.81, (s, 3H), 1.70 (s, 3H), 1.61 (s, 3H), 1.17 (s, 3H), 1.03 (s, 3H) ppm.

EXAMPLE 17
2-(2,3-Dimethyl-but-2-enyl)-2,6-dimethyl-cyclohexanone

Odor: fresh, grapefruit, bergamot, lavender

This compound was prepared according to example 1. Excessive hydrogenation resulted in a mixture of 2 diastereomers in a ratio of 3:1. Main isomer: $^1$H-NMR (400 MHz, CDCl$_3$): 2.89 (sept, J=6.4 Hz, 1H, 6-H), 2.58 (d, J=13.8 Hz, 1H, 1'-Ha), 2.43 (d, J=13.8 Hz, 1H, 1'-Hb), 2.11–1.25 (m, 6H), 1.61 (bs, 6H), 1.46 (s, 3H), 1.01 (d, J=6.4 Hz, 3H, 6-CH$_3$), 0.95 (s, 3H, 2-CH$_3$) ppm. GC/MS (EI): 208 (M$^+$, 3), 126 (100), 111 (29), 83 (43), 67 (10), 55 (48), 41 (36). IR (ATR): 2967s, 2931s, 2867s, 1704s, 1453s, 1375m, 1124m, 997m cm$^{-1}$.

EXAMPLE 18

| Green grapefruit floral composition for cosmetics | |
|---|---|
| | parts per weight |
| Benzyl acetate extra | 35 |
| Geranyl acetate | 1 |
| cis-3-Hexenyl acetate | 6 |
| Terpenyl acetate | 3 |
| Agrumex | 35 |
| Hexyl cinnamic aldehyde | 55 |
| Boisambrene forte (10% DPG) | 2 |
| Ethylene brassylate | 20 |
| Dimethyl benzyl carbinyl butyrate | 5 |
| Ethyl capronate (10% DPG) | 7 |
| Cetone V (10% DPG) | 1 |
| Citronellol extra | 40 |
| Cyclal C | 18 |
| Allyl Cyclohexanepropionate | 5 |
| γ-Decalactone (10% DPG) | 15 |
| Dihydromyrcenol | 125 |
| Dipropylene glycol | 70 |
| β-Ionone | 65 |
| Phenoxyethyl isobutyrate | 152 |
| Lilial | 80 |
| Linalool | 100 |
| Ethyl 2-methyl butyrate | 10 |
| Allyl oenanthate | 25 |
| Orange Ess. Florida | 60 |
| Verdyl propionate | 20 |
| Hexyl salicylate | 15 |
| Terpineol | 10 |
| 1,2,6-Trimethyl-6-(3-methyl-but-2-enyl)-cyclohex-2-enol | 20 |
| | 1000 |

In this green grapefruit accord, 1,2,6-trimethyl-6-(3-methyl-but-2-enyl)-cyclohex-2-enol adds freshness and volume to the perfume and pushes the hesperidic orange-grapefruit aspect. Its long lasting effect helps to keep these properties over time.

EXAMPLE 19

A fougère-hesperidic perfume composition

| | parts per weight |
|---|---|
| Acetyl linalool synth. | 30 |
| Allyl amyl glycolate | 5 |
| Ambrettolide | 15 |
| Ambrofix | 5 |
| Armoise ess. | 5 |
| Bergamote ess. | 80 |
| Calone 10% DPG | 25 |
| Lemon ess. italie | 30 |
| Coumarine crist. | 20 |
| Cyclohexal | 15 |
| Dihydro myrcenol | 85 |
| Dipropylene glycol | 100 |
| Ebanol | 20 |
| Ethyl linalool | 50 |
| Evernyl | 10 |
| Fixolide | 65 |
| Florhydral | 5 |
| Geranium ess. | 10 |
| Givescone | 5 |
| Hedione | 110 |
| ISO E Super | 65 |
| Isoraldeine 95 | 10 |
| Labienoxime 10% DPG | 10 |
| Lavander ess. | 15 |
| Methyl pampelmousse | 65 |
| Radjanol | 40 |
| Sandalore | 15 |
| Clary sage ess. | 5 |
| Stemone | 10 |
| Tricyclal 10% DPG | 15 |
| Tropional | 40 |
| 1,2,6-Trimethyl-6-(3-methyl-but-2-enyl)-cyclohex-2-enol | 20 |
| | 1000 |

The grapefruit character of this fougere accord is well accentuated by 1,2,6-trimethyl-6-(3-methyl-but-2-enyl)-cyclohex-2-enol especially in the dry down note. The compound harmonizes top and middle note and goes well together with the marine and woody facets of this perfume.

EXAMPLE 20

Blueberry flavor for a yoghurt

| | parts per weight |
|---|---|
| Geranium oil bourbon FG | 0.30 |
| Bergamot oil peel Italy | 0.20 |
| Ylang ylang oil rectified | 0.05 |
| Linalool | 2.00 |
| Orris resin (water soluble) | 0.10 |
| alpha-Terpineol | 4.00 |
| iso-Pentanol | 0.70 |
| Geraniol | 0.10 |
| Acetic acid | 4.00 |
| Acetoin (nature identical BV) | 0.06 |
| Eucalyptol | 0.30 |
| Ethyl hexanoate | 1.00 |
| Ethyl iso-pentanoat | 20.00 |
| Ethyl acetate | 20.00 |
| iso-Pentyl iso-pentanoate | 12.00 |
| Butyric acid | 0.05 |
| Ethyl butyrate | 0.50 |
| Ethyl 2-methyl butyrate | 2.00 |
| 2-Methyl butyric acid | 0.50 |
| Butyl acetate | 0.10 |

-continued

Blueberry flavor for a yoghurt

| | parts per weight |
|---|---|
| cis-3-Hexenol | 0.50 |
| iso-Pentyl acetate | 3.50 |
| Diacetyl | 0.06 |
| Methyl cinnamate | 0.70 |
| Ethyl lactate | 1.00 |
| Tannic acid | 0.05 |
| gamma-Nonalactone | 0.25 |
| Methyl iso-pentanoate | 5.00 |
| trans-2-Hexenal | 0.50 |
| 3-trans-Hexenoic acid | 0.20 |
| Propylene glycol USP | 919.28 |
| 1,2,6-Trimethyl-6-(3-methyl-but-2-enyl)-cyclohex-2-enol | 1.00 |
| | 1000.00 |

1,2,6-Trimethyl-6-(3-methyl-but-2-enyl)-cyclohex-2-enol adds a natural fresh note to the flavor. The compound further boosts the blueberry-fruity taste in a yoghurt.

EXAMPLE 21

Pink grapefruit flavor for a yoghurt

| | parts per weight |
|---|---|
| Ethanol | 805.2 |
| Nootkatone (nature identical BV) | 4.8 |
| Orange oil 7.8-fold Brazil | 34.0 |
| Juniper berry extract $CO_2$ | 10.0 |
| Orange essence oil 10-fold Brazil | 47.0 |
| Orange oil 5-fold Palestine | 50.0 |
| Grapefruit base | 48.0 |
| 1,2,6-Trimethyl-6-(3-methyl-but-2-enyl)-cyclohex-2-enol | 1.0 |
| | 1000.0 |

In this pink grapefruit flavor 1,2,6-trimethyl-6-(3-methyl-but-2-enyl)-cyclohex-2-enol increases freshness and harmonizes well with its fruity-hesperidic note. The compound gives volume and a more natural taste in a yoghurt.

What is claimed is:

1. A compound of the formula (I)

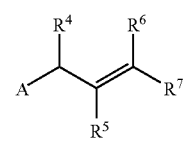

comprising less than 18 carbon atoms
wherein A is a residue of the formula II, III or IV

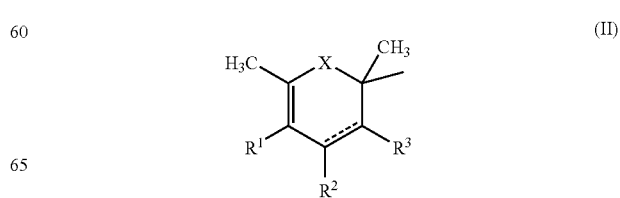

-continued

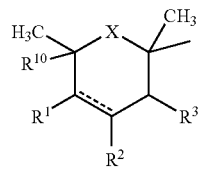
(III)

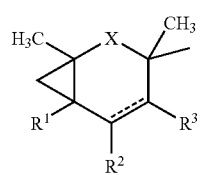
(IV)

wherein
$R^1$–$R^6$ are independently hydrogen or a methyl group, $R^7$ is a methyl or ethyl group, and $R^8$ and $R^7$ are capable of forming together a furan ring;

X is either a carbonyl group or $CR^8OR^9$, wherein $R^8$ is hydrogen, methyl, ethyl, propyl, ethynyl or vinyl and $R^9$ is hydrogen, methyl or ethyl;

$R^{10}$ is hydrogen, methyl or ethyl; the dotted line in formula (II) is a bond only if X is $OR^8R^9$; and the dotted line in formula (III) and the dotted line in formula (IV) optionally is a bond.

2. The compound of formula (I) according to claim 1 wherein A is a residue of formula (IIa)

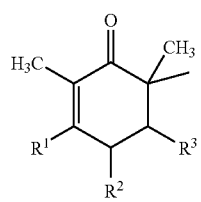
(IIa)

wherein $R^1$–$R^3$ are independently hydrogen or a methyl group.

3. The compound of formula (I) according to claim 1 wherein A is a residue of formula (IIb)

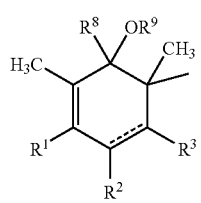
(IIb)

wherein
$R^1$–$R^3$ are independently hydrogen or a methyl group;
$R^8$ is hydrogen, methyl, ethyl, propyl, ethynyl or vinyl and $R^9$ is hydrogen, methyl or ethyl;
and the dotted line in formula (IIb) optionally is a bond.

4. The compound of formula (I) according to claim 1 wherein the compound is
1,2,6trimethyl-6-(3-methyl-but-2-enyl)-cyclhex-2-enol.

5. The compound of formula (I) according to claim 1 wherein the compound is selected from the group consisting of 2,6-dimethyl-6-(3-methyl-but-2-enyl)-cyclohex-2-enol; 2,6-dimethyl-6-(3-methyl-but-2-enyl)-1-vinyl-cyclohex-2-enol; 2,6-dimethyl-1-ethyl-6-(3-methyl-but-2-enyl)-cyclohex-2-enol and 2-(2,3-dimethyl-but-2-enyl)-2,6-dimethyl-cyclohexanone.

6. The compound of formula (I) according to claim 1, wherein the compound is 2,8-dimethyl-6-(3-methyl-but-2-enyl)-cyclohex-2-enone.

7. The compound of formula (I) according to claim 1, wherein the compound is 6-methoxy-1,5,(-trimethyl-5-(3-methyl-but-2-enyl)-cyclohexene.

8. An organoleptic composition comprising a compound according to claim 1.

9. An organoleptic composition according to claim 8 comprising additional fragrance ingredients.

10. An organoleptic composition according to claim 8 comprising additional flavor ingredients.

11. A consumer product selected from the group which includes body care and cosmetic products including cream, shampoo, soap, sun cream, household products including detergents, household cleaners, fabric softener's, food and beverage products, and fine perfumes comprising a compound according to claim 1.

12. A food or beverage product comprising a compound according to claim 1.

13. A method of flavoring or fragrancing a product by adding at least one compound according to claim 1 to the product.

14. A method for preparing compounds of formula (I)

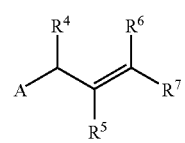
(I)

comprising less than 18 carbon atoms
wherein A is a residue of the formula (II)

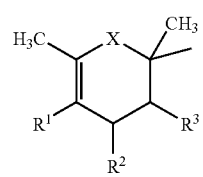
(II)

wherein
$R^1$–$R^6$ are independently hydrogen or a methyl group, $R^7$ is a methyl or ethyl group, and $R^5$ and $R^7$ are capable of forming together a phenyl or a furan ring; and
X is a carbonyl group;
said method comprises
a) reacting a phenol derivative of the formula (V)

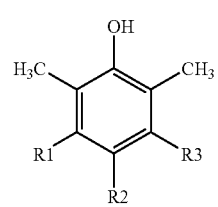
(V)

wherein $R^1$–$R^3$ are independently hydrogen or a methyl group;
under phase transfer conditions to the corresponding alkylated dienone of the formula (VI)

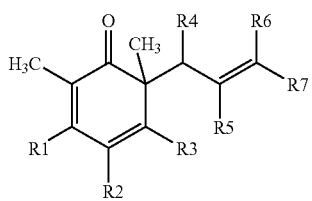

wherein $R^1$–$R^7$ are independently hydrogen, methyl, or ethyl group; and b) selectively reducing the dienone of the formula (VI) by using a transition metal catalyst.

15. A compound selected from the group consisting of:
2,4,6-trimethyl-8-(3-methyl-but-2-enyl)-cyclohex-2-enone;
2,3,6-trimethyl-8-(3-methyl-but-2-enyl)-cyclohex-2-enone;
6-benzyl-2,6-dimethyl-cyclohex-2-enone;
1,3-dimethyl-3-3(3-methyt-but-2-enyl)-bicyclo[4.1.0]heptan-2-one;
2,2,6-trimethyl-8-(3-methyl-but-2-enyl)-cyclohex-3-enone;
2,6dimethyl-2-(3-methyl-but-2-enyl)-cyclohexanone;
1,2,4,6-tetramethyl-8-8(3-methyl-but-2-enyl)-cyclohex-2-enol;
1,2,3-trimethyl-3-(3-methyl-but-2-enyl)-bicyclo[4.1.0]heptan-2-ol;
2,6-dimethyl-6-(3-methyl-but-2-enyl)-cyclohex-2,4-dienone; and,
1,2,6-trimethyl-8-(3-methyl-but-2-enyl)-cyclohexa-2,4-dienol.

* * * * *

UNITED STATES PATENT AND TRADEMARK OFFICE
CERTIFICATE OF CORRECTION

PATENT NO. : 7,078,570 B2
APPLICATION NO. : 10/433342
DATED : July 18, 2006
INVENTOR(S) : Andreas Goeke It is certified that error appears in the above-identified patent and that said Letters Patent is hereby corrected as shown below:

Column 5, Line 52 "was stirred for 45 min. The mixture was cooled to 50° C.,"
should read -- was stirred for 45 min. The mixture was cooled to 5° C., --

Column 5, Line 54 "during 1.5 h keeping the temperature at 50° C. The mixture"
should read -- during 1.5 h keeping the temperature at 5° C. The mixture --

Column 13, Line 19 "is a methyl group or ethyl group, and $R^8$ and $R^7$ are capable"
should read -- is a methyl group or ethyl group, and $R^5$ and $R^7$ are capable --

Column 13, Line 26 "formula (II) is a bond only if X is $OR^8R^9$; and the"
should read -- formula (II) is a bond only if X is $CR^8OR^9$; and the --

Column 14, Line 5 "wherein the compound is 2,8-dimethyl-6-(3-methyl-but-2-"
should read -- wherein the compound is 2,6-dimethyl-6-(3-methyl-but-2- --

Column 14, Line 8 "wherein the compound is 6-methoxy-1,5,(-trimethyl-5-(3-"
should read -- wherein the compound is 6-methoxy-1,5,6-trimethyl-5-(3- --

Column 14, Line 15 "A consumer product selected from the group which includes body care and cosmetic products including cream, shampoo, soap, sun cream, household products including detergents, household cleaners, fabric softener's, food and beverage products, and fine perfumes comprising a compound according to claim 1."
should read --A consumer product selected from the group consisting of body care and cosmetic products comprising cream, shampoo, soap, sun cream; household products comprising detergents, household cleaners, and fabric softeners; food and beverage products, and fine perfumes comprising a compound according to claim 1. --

Column 15, Line 17 "2,4,6-trimethyl-8-(3-methyl-but-2-enyl)-cyclohex-2-enone;"
should read -- 2,4,6-trimethyl-6-(3-methyl-but-2-enyl)-cyclohex-2-enone; --

Column 15, Line 18 "2,3,6-trimethyl-8-(3-methyl-but-2-enyl)-cyclohex-2-"
should read -- 2,3,6-trimethyl-6-(3-methyl-but-2-enyl)-cyclohex-2- --

Column 16, Line 5 "2,2,6-trimethyl-8-(3-methyl-but-2-enyl)-cyclohex-3-"
should read -- 2,2,6-trimethyl-6-(3-methyl-but-2-enyl)-cyclohex-3- --

Column 16, Line 8 "1,2,4,6-tetramethyl-8-8(3-methyl-but-2-enyl)-cyclohex-"
should read -- 1,2,4,6-tetramethyl-6-6-(3-methyl-but-2-enyl)-cyclohex- --

UNITED STATES PATENT AND TRADEMARK OFFICE
CERTIFICATE OF CORRECTION

PATENT NO. : 7,078,570 B2
APPLICATION NO. : 10/433342
DATED : July 18, 2006
INVENTOR(S) : Andreas Goeke It is certified that error appears in the above-identified patent and that said Letters Patent is hereby corrected as shown below:

Column 16, Line 15 "1,2,6-trimethyl-8-(3-methyl-but-2-enyl)-cyclohexa-2,4-"
should read -- 1,2,6-trimethyl-6-(3-methyl-but-2-enyl)-cyclohexa-2,4- --

Signed and Sealed this

Third Day of April, 2007

JON W. DUDAS
*Director of the United States Patent and Trademark Office*